(12) United States Patent
Ishii

(10) Patent No.: US 6,183,427 B1
(45) Date of Patent: Feb. 6, 2001

(54) DOZING PREVENTIVE DEVICE AND ITS METHOD

(75) Inventor: Shigeharu Ishii, Tokyo (JP)

(73) Assignee: Thinky Corp., Tokyo (JP)

( * ) Notice: Under 35 U.S.C. 154(b), the term of this patent shall be extended for 0 days.

(21) Appl. No.: 09/155,800

(22) PCT Filed: Feb. 6, 1998

(86) PCT No.: PCT/JP98/00493
§ 371 Date: Jan. 29, 1999
§ 102(e) Date: Jan. 29, 1999

(87) PCT Pub. No.: WO98/34666
PCT Pub. Date: Aug. 13, 1998

(30) Foreign Application Priority Data

Jun. 2, 1997 (JP) .................................................. 9-023369

(51) Int. Cl.[7] ..................................................... A61H 1/00
(52) U.S. Cl. ............................... 601/46; 601/67; 601/69; 601/70; 601/72; 601/139
(58) Field of Search .................................. 601/46, 47, 51, 601/58, 67, 68, 69, 70, 72, 73, 80, 84, 97, 139, 140–142, 89; 433/118, 122; 310/15; 318/119; 15/24, 110

(56) References Cited

U.S. PATENT DOCUMENTS

| | | | |
|---|---|---|---|
| 2,422,639 | * 6/1947 | Wenander | 74/87 |
| 3,033,197 | * 5/1962 | Barckley | 601/141 |
| 3,363,623 | * 1/1968 | Atwell | 601/72 |
| 3,563,233 | * 2/1971 | Bodine | 601/72 |
| 3,623,481 | * 11/1971 | Curran | 601/74 |
| 3,978,852 | * 9/1976 | Annoni | 601/142 |
| 4,219,619 | * 8/1980 | Zarow | 433/118 |
| 4,827,551 | * 5/1989 | Maser et al. | 15/24 |
| 5,030,098 | * 7/1991 | Branford | 433/215 |

* cited by examiner

*Primary Examiner*—Justine R. Yu
(74) *Attorney, Agent, or Firm*—Liniak, Berenato Longacre & White (57) ABSTRACT

A dozing preventive device and its method are disclosed, in which the user does not have to move to a specific place for dozing prevention, and neighboring people are not disturbed. The dozing preventive device is small and is simple in its construction so that the user does not have to use his hand for supporting the device. The dozing preventive device comprises: a contacting portion directly contacting with the teeth of a user; a vibration mechanism for vibrating the contacting portion; a power supply for driving the vibration mechanism; and a housing case for accommodating the vibration mechanism and the power supply as well as for supporting the contacting portion. The dozing preventive device is brought into contact with the teeth of a user so that the vibration is transmitted to the user's brain, thereby preventing the user from sleeping.

11 Claims, 11 Drawing Sheets

DOZING PREVENTIVE DEVICE AND ITS METHOD

TECHNICAL FIELD

The present invention relates to a dozing preventive device and its method which acts on a user's brain by transmitting a vibration through his teeth.

BACKGROUND ART

A known method for dozing prevention during driving or attending a meeting is chewing gum or drinking medicine such as caffeine to keep one's brain awaken.

Another method is for stimulating one's face by washing in cold water.

A dozing preventive device is also known. The device is set to be positioned at one's ear so that when the user inclines his head at more than a predetermined angle, the nodding movement is detected and a beep or buzzing sound is generated. The user is therefore awaken by this sound.

DISCLOSURE OF THE INVENTION

In the above known methods, however, various problems exist. For example, dozing prevention is not always achieved by chewing gum or drinking medicine. Further, it is not polite to attend a meeting while chewing gum in front of other attendants.

As to washing face in cold water, if one is involved in an operation such as driving, the driver may have to drive his car to a particular place where he can use a water tap. When the driver is driving on a superhighway, he may have to drive to a next parking area. Meanwhile, when the driver is driving on a town road, he has to drive to a park nearby or the like place for a water tap.

As to the above dozing preventive device, since the beep sound is produced after the user's nodding movement is detected, that is to say, the device actuates after the user actually falls into a sleep, the awaking timing acting on the user's brain tends to be delayed. This is serious when the user is involved in a dangerous operation such as driving a vehicle.

In this dozing preventive device, a possible misoperation occurs due to the nodding movement of the user such as when he reads documents in a meeting. The dozing preventive device also has a drawback in that the beep sound to be produced annoys neighboring people.

With the aforementioned drawbacks of the prior art in view, the present invention seeks to provide a dozing preventive device and its method for securely preventing the user from sleeping, in which a vibration is transmitted through the user's teeth to his brain. The inventive device is simple in its construction, and it does not require the user to move to a specific place, and further it does not produce a beep or buzzing sound which annoys neighboring people.

According to the present invention, there is provided a dozing preventive device comprising:
a contacting portion directly contacting with the teeth of a user;
a vibration mechanism for vibrating the contacting portion;
a power supply for driving the vibration mechanism; and
a housing case for accommodating the vibration mechanism and the power supply as well as for supporting the contacting portion.

The vibration mechanism of the above dozing preventive device may be positioned within the housing case adjacent to the contacting portion and an electric power supply connector may be connected between one end of the vibration mechanism and the power supply.

Also, the vibration mechanism may comprise a driven portion having a rotational shaft and a stroke portion provided on the rotational shaft, and a driving portion for driving the driven portion, thereby vibration occurs when the stroke portion continuously or intermittently hits the contacting portion.

The contacting portion and the stroke portion may be provided with protrusions for intermittent contact therebetween so that vibration frequency of the contacting portion is determined by the number of such protrusions.

Further, the front end of the housing case may be deformed to form a contacting portion, and the rear end of the contacting portion may be provided with an accommodation space for said vibration mechanism.

According to the present invention, there is also provided a dozing preventing method using the above dozing preventive device, wherein the contacting portion with a predetermined vibration frequency is brought into contact with the teeth of a user so that the vibration is transmitted to the user's brain.

Further, there is provided a dozing prevention method using the above dozing preventive device, wherein the stroke portion provided on the rotational shaft continuously or intermittently contacts with the contacting portion during the rotational movement of the rotational shaft, and the contacting portion vibrating is brought into contact with the teeth of a user so that the vibration is transmitted to the user's brain.

BRIEF DESCRIPTION OF DRAWINGS

Preferred embodiments of the present invention may be described with reference to the following drawings, in which.

BEST MODE FOR CARRYING OUT THE INVENTION

Figure 1:
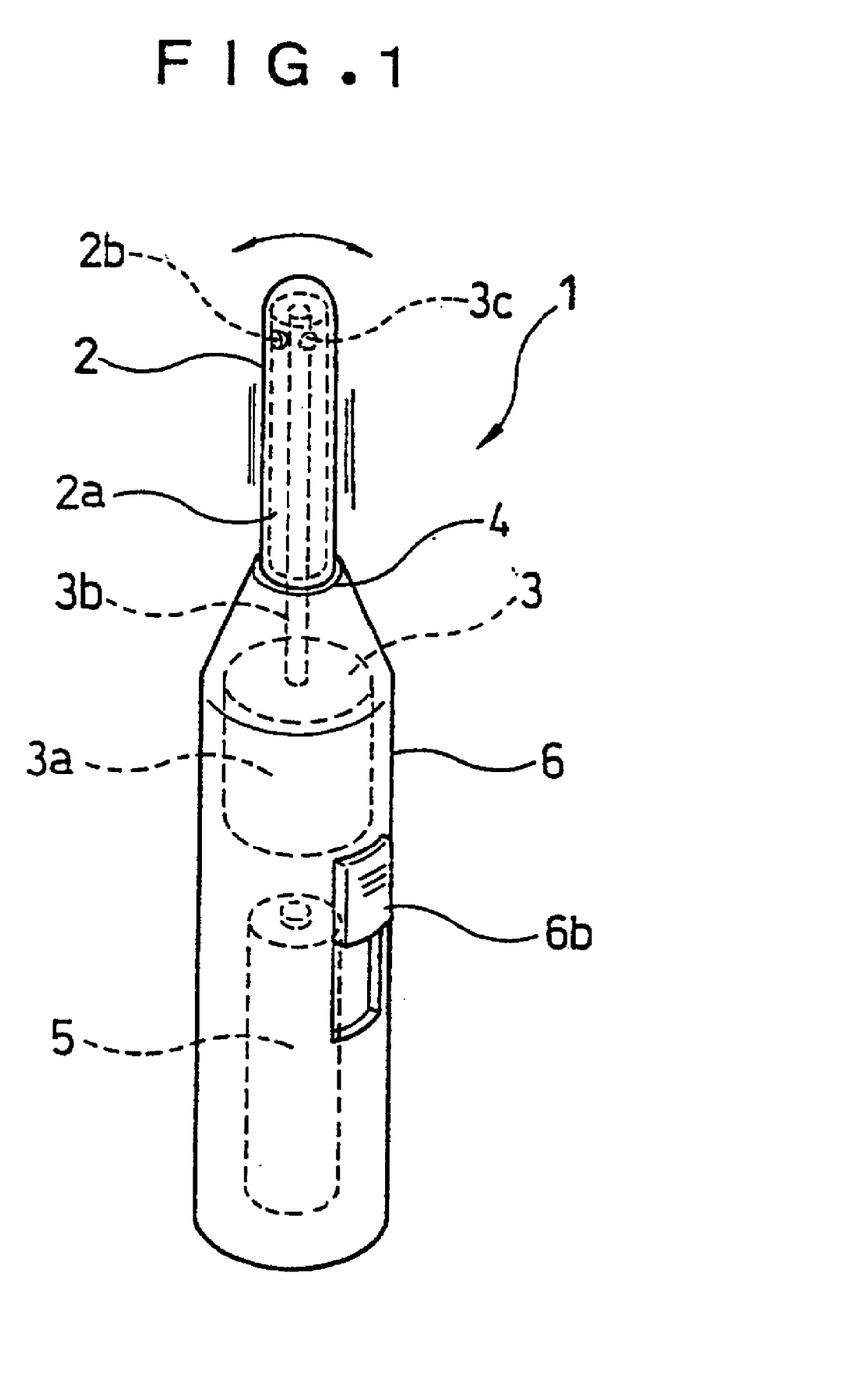
FIG. 1 is a perspective view showing a dozing preventive device according to the present invention.

Referring now to FIG. 1, a dozing preventive device 1 comprises a contacting portion 2 directly contacting with the teeth of a user, a vibration mechanism 3 for vibrating the contacting portion 2, a power supply 5 for driving the vibration mechanism 3, and a housing case 6 for accommodating the vibration mechanism 3 and the power supply 5 as well as for supporting the contacting portion 2.

Figure 2:
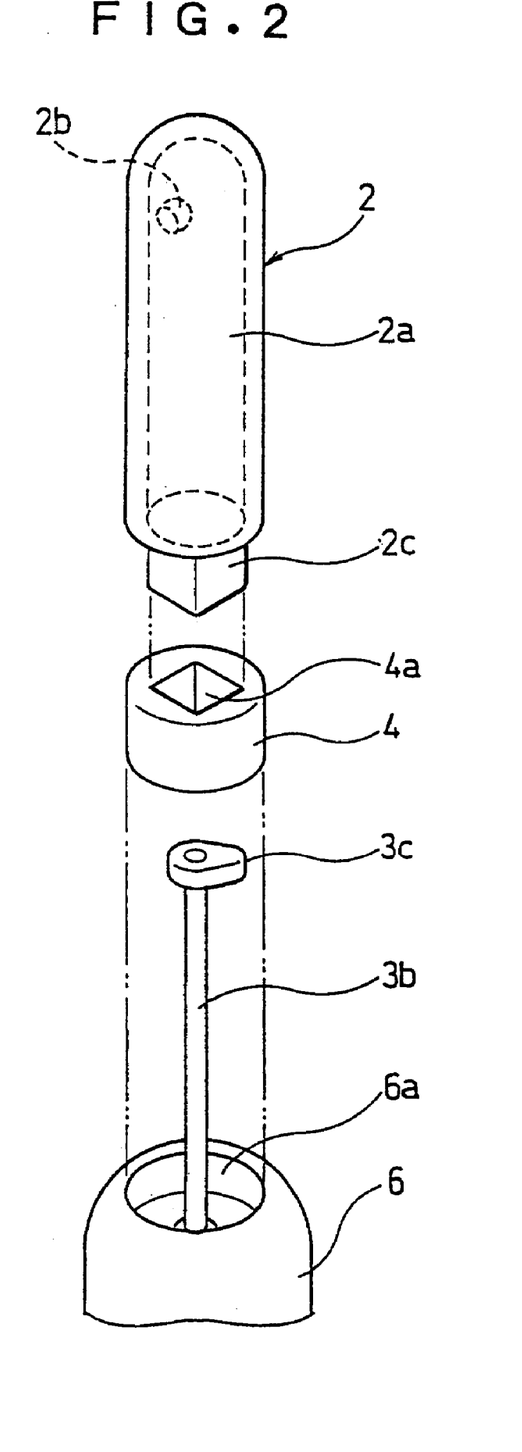
FIG. 2 is an exploded perspective view explaining the subject construction of the dozing preventive device.

As shown in FIG. 2, the contacting portion 2 comprises a main body 2a, a protrusion 2b provided at a predetermined position on the inner surface of the main body 2a, and an engaging portion 2c engageable with the upper end of the housing case 6. The engaging portion 2c of the contacting portion 2 is attached to the housing case 6 through a mounting rubber 4 having an engaging opening 4a. The engaging portion 2c is of the shape corresponding to the engaging opening 4a, and is preferably formed to have a polygonal outer profile (square in this figure) so as to prevent the rotational movement of the contacting portion 2. The mounting rubber 4 is fitted in an upper recess 6a of the housing case 6. Although the mounting rubber 4 has a tubular profile, the rotation of the mounting rubber 4 can be prevented due to its greater friction.

Referring to FIGS. 1 and 2, the vibration mechanism 3 comprises a driving motor 3a as a driving portion, a rotational shaft 3b for transmitting the rotational movement of the driving motor 3a, and a cam provided at the front side of the rotational shaft 3b. The rotational shaft 3b extends within the main body 2a of the contacting portion 2, and the cam 3b is rotatable within the main body 2a. When the driving motor 3a is actuated and the rotational shaft 3b rotates, the cam 3c is rotated within the main body 2a of the contacting portion 3. The cam 3c then hits the protrusion 2b of the main body 2a intermittently, thereby generating a vibration.

The driving motor 3a is driven by a battery as a power supply 5. The battery is accommodated within the housing case 6. The housing case 6 is provided with a switch 6b for the on-and-off control of the driving motor 3a. The switch 6b also ensures two or three steps of adjustment for the rotational speed of the driving motor 3a.

Figure 3:
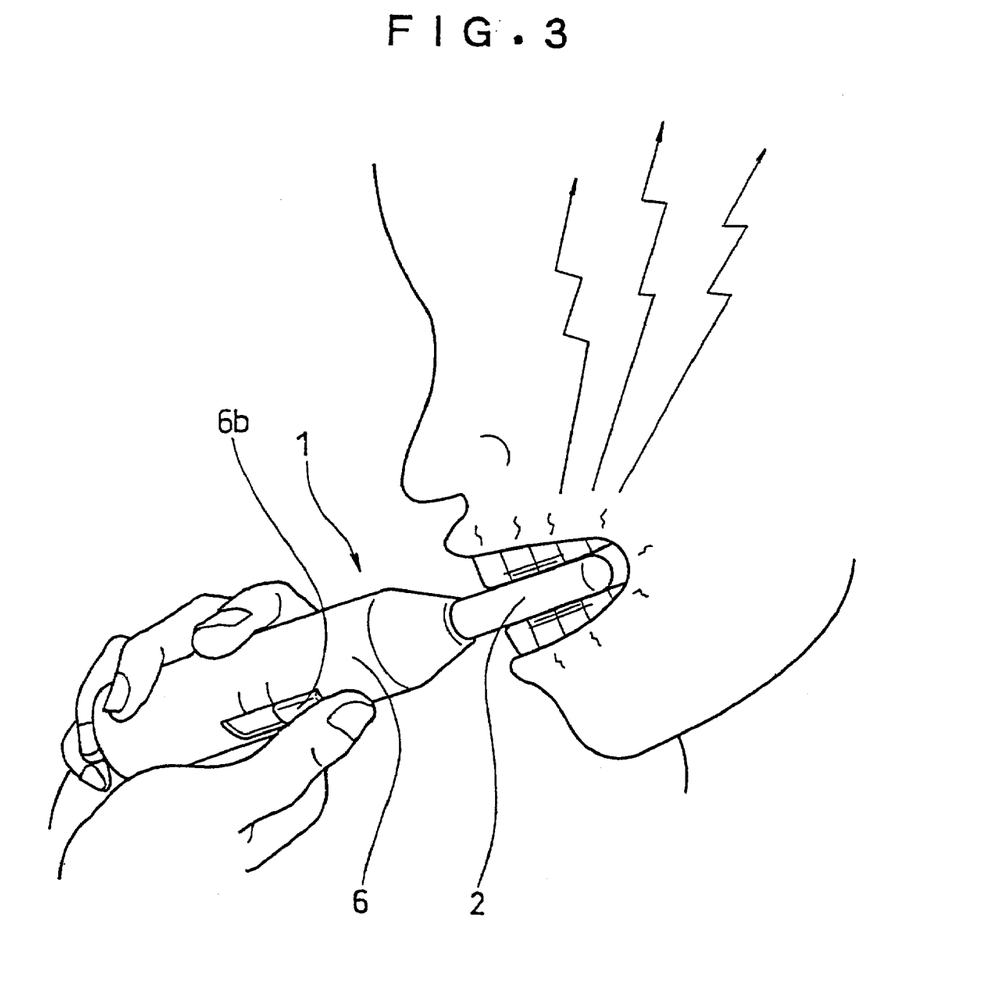
FIG. 3 is a perspective view explaining the state of use of the dozing preventive device.

Manner of operation of the dozing preventive device 1 will now be described with reference to FIG. 3. If one becomes sleepy while being involved in a dangerous operation such as driving, he grips the housing case 6 of the dozing preventive device 1 and moves it until the contacting portion 2 thereof is brought into contact with his teeth. When he turns on the switch 6b, vibration of the contacting portion 2 is transmitted through the teeth to his brain, thereby preventing him from sleeping.

Figure 8A:
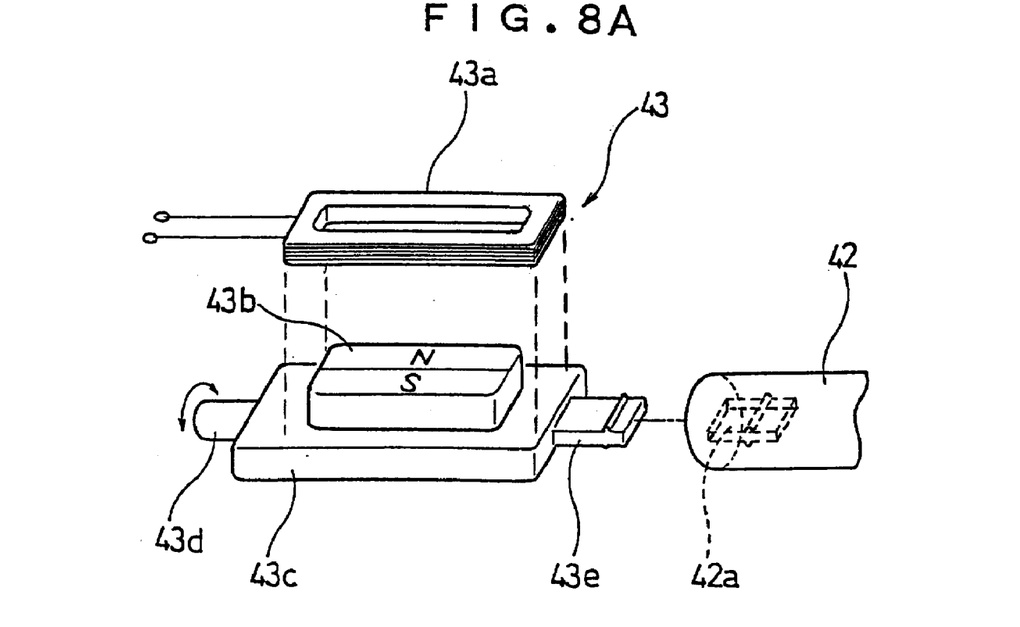
FIG. 8(a) is an exploded perspective view showing the subject construction of still another vibration mechanism.
Figures 8B, 8C:
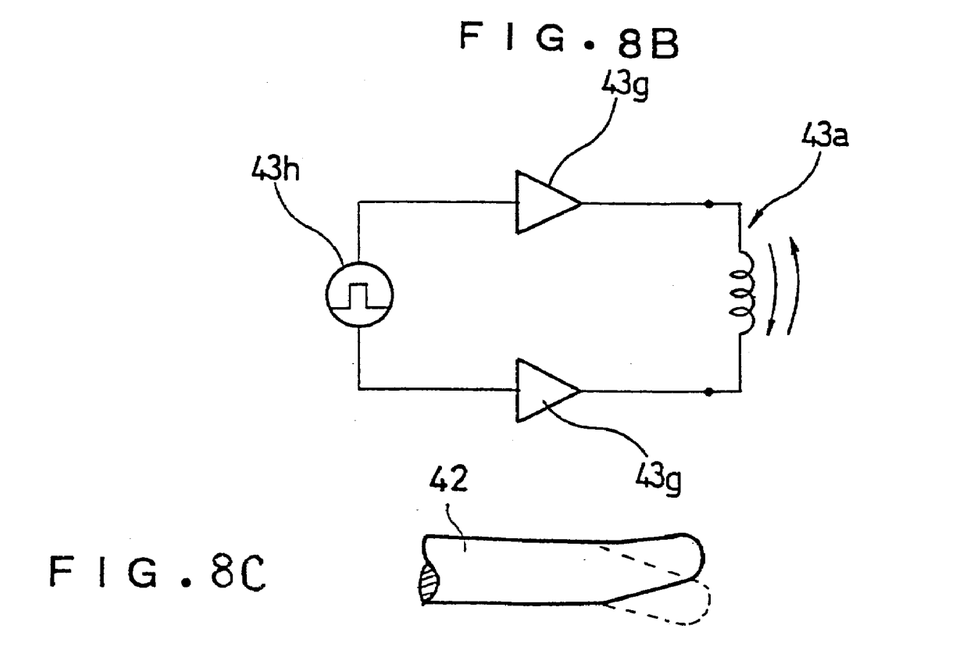
FIG. 8(b) is a circuit diagram of the vibration mechanism shown in FIG. 8(a)
FIG. 8(c) is a side view showing the subject construction of its stroke portion.

The contacting portion 2 is preferably formed to be reciprocally movable to the axis thereof so as to provide a continuous and effective vibration to the user's teeth However, the contacting portion 2 may be bent to a predetermined angle, such as shown in FIG. 8(c), so that the stroking force to hit the user's teeth is increased.

Figure 4A:
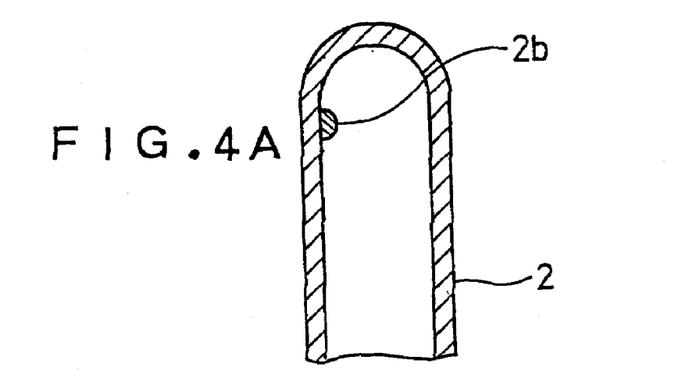
FIG. 4A is a sectional view showing the subject construction of a contacting portion.
Figure 4B:
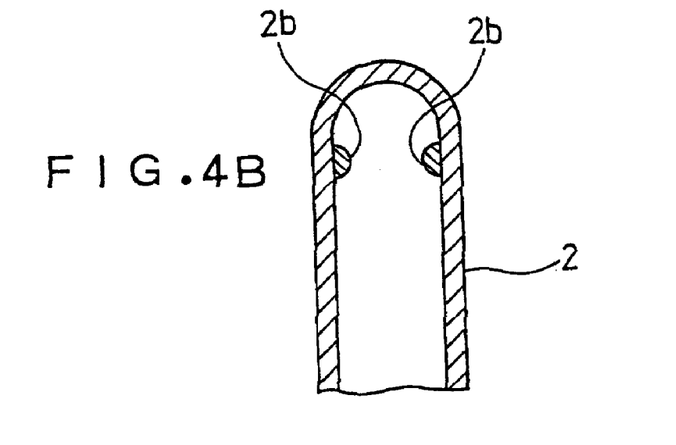
FIGS. 4B & 4C are sectional views of alternate contacting portions.
Figure 4C:
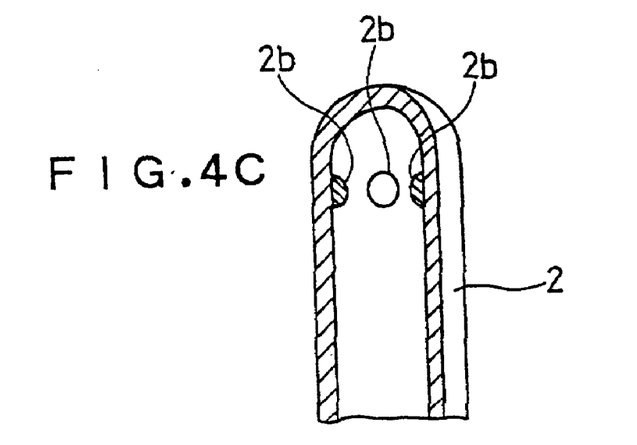

Vibration frequency of the contacting portion 2 is controlled by changing the rotational speed of the driving motor 3a. However, as shown in FIG. 4, vibration frequency may vary by the number of protrusions provided on the inner surface of the contacting portion 2. With the provision of two protrusions 2b, such as shown in FIG. 4(b), vibration frequency may be doubled. As shown in FIG. 4(c), provision of three protrusions 2b may of course be possible. In these examples, protrusions 2b are formed around the same inner peripheral surface of the contacting portion 2. However, protrusions 2b may be provided at different levels. In such case, a plurality of cams 3c are provided on the rotational shaft 3b at the different levels corresponding to these protrusions 2b so that the cams 3c and the protrusions 2b interact to each other upon rotation of the rotational shaft 3b.

Another embodiment of a dozing preventive device according to the present invention will now be described.

Figure 5A:
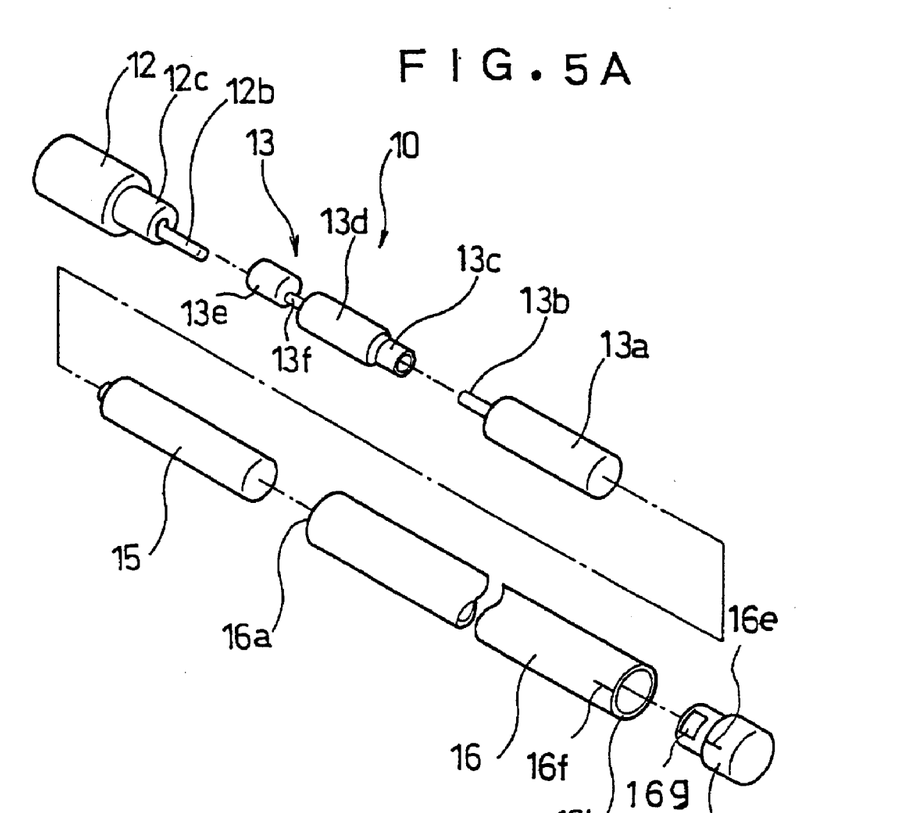
FIG. 5(a) is an exploded perspective view showing another dozing preventive device according to the present invention.
Figure 5B:
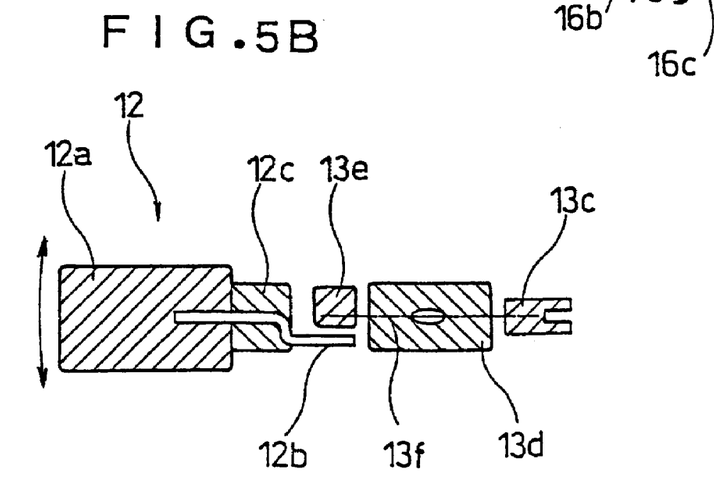
FIG. 5(b) is a sectional view showing a contacting portion and the subject construction of a vibration mechanism of the dozing preventive device shown in FIG. 5(a)

Referring to FIGS. 5(a) and (b), the dozing preventive device 10 comprises a contacting portion 12 directly contacting with the teeth of a user, a vibration mechanism 13 for vibrating the contacting portion 12, a driving motor 13a as a driving portion for the vibration mechanism 13, a power supply 15 for driving the driving motor 13a, and a housing case 16 for accommodating the contacting portion 12, the vibration mechanism 13, the driving motor 13a and the power supply 15. The size of the dozing preventive device 10 is almost same as a cigarette.

As shown in FIG. 5(b), the contacting portion 12 includes a main body 12a directly contacting with the teeth of a user, an engaging portion 12c provided at the base portion of the main body 12a and engageable with one end of the housing case 16, and a protrusion 12b supported by the main body 12a and the engaging portion 12c and extending at an offset position from the engaging portion 12c.

For a security reason, the main body 12a of the contacting portion 12 is made from a material such as polyethylene. Meanwhile, the engaging portion 12c is made from a material having higher friction such as rubber or synthetic rubber so as to ensure smooth and reliable engagement with the housing case 16. The protrusion 12b is preferably formed of a steel wire (piano wire) or a stainless wire, and is offset from the center of the main body 12a.

The vibration mechanism 13 comprises a coupling 13c attached to a rotational shaft 13b of the driving motor 13a, a linear axial portion 13f provided at the coupling 13c and formed of a steel wire or a stainless wire, a rotational bearing 13d rotatably supporting the linear axial portion 13f, and a cam 13e as a stroke portion provided at the front side of the linear axial portion 13f.

When the driving motor 13a is actuated and the rotational shaft 13b rotates, the cam 13e is rotated through the coupling 13c and the linear axial portion 13f. The cam 13e then hits the protrusion 12b of the contacting portion 12, thereby generating a vibration at the main body 12a.

Since the linear axial portion 13f is to some extent flexible, rotation of the cam 13e is not disturbed when the cam 13e hits the protrusion 12b of the contacting portion 12.

The housing case 16 is formed in the shape of a tube, the front side of which is provided with a front opening support 16a engageable with the engaging portion 12c of the contacting portion 12, while the rear side of which is provided with a rear opening support 16b for supporting a cap 16c. The cap 16c is rotatable relative to the housing case 16. The cap 16c includes a connecting peace 16g for the on-and-off adjustment of the power supply 15. When the cap 16c is rotated and the "On" mark 16e provided on the cap 16c is in mating relation with the corresponding "On" mark 16f at the rear side of the housing case 16, the power supply switch of the power supply 15 is on. The power supply 15 is a smaller-sized battery such as a UM-4 type buttery or a button buttery so as to be accommodated within the housing case 16.

The dozing preventive device 10 is kept in a user's mouth so that when the user becomes sleepy, he turns on the switch by rotating the cap 16c relative to the housing case 16. For example, when the user drives a car, he puts the dozing preventive device 10 in his mouth like a cigarette.

When the driving motor 13a is actuated and the rotational shaft 13b rotates, the cam 13e is rotated through the coupling 13c and the linear axial portion 13f. The cam 13e then hits the protrusion 12b of the contacting portion 12, thereby generating a vibration at the main body 12a. Since the dozing preventive device 10 is kept in the user's mouth with the main body 12a contacting to the user's teeth, the vibration generated is transmitted through the teeth to the user's brain so as to keep the user awaken.

Referring now to FIG. 6, another vibration mechanism will be described.

Figure 6A:
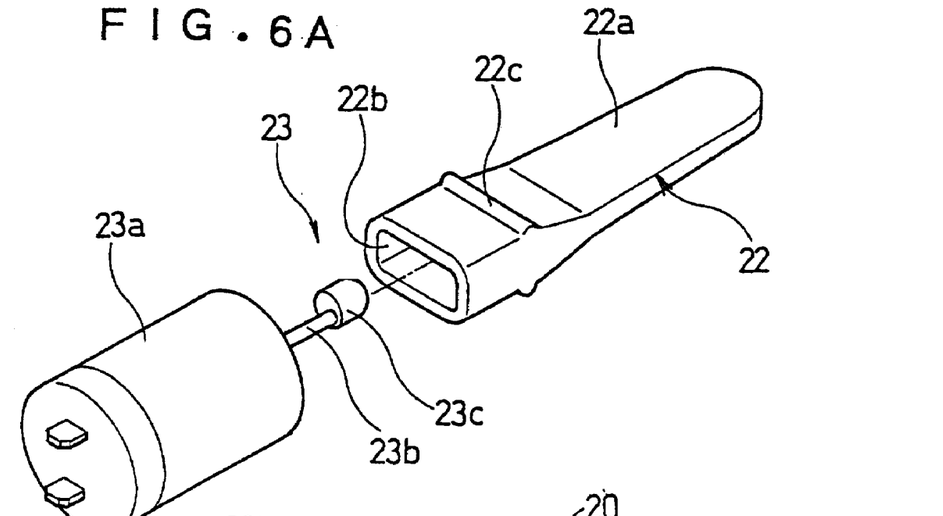
FIG. 6(a) is an exploded perspective view showing the subject construction of another vibration mechanism.
Figure 6B:
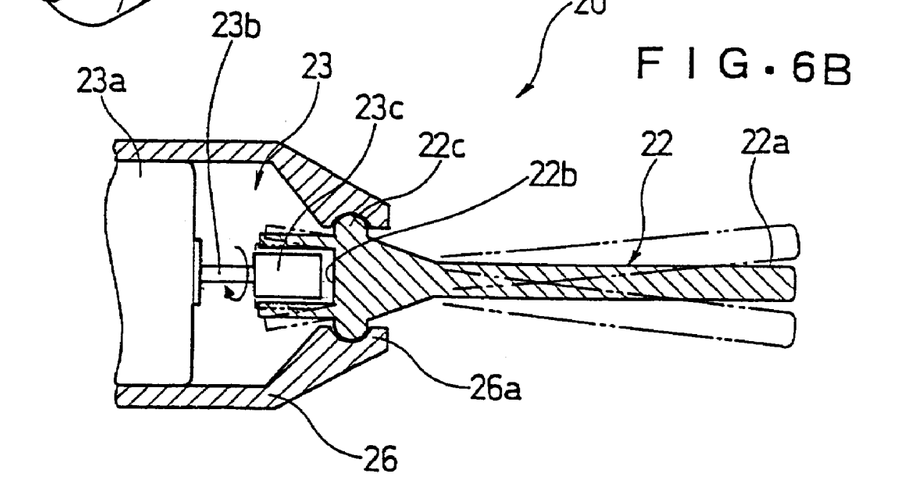
FIG. 6(b) is a sectional view showing the subject construction of the vibration mechanism shown in FIG. 6(a), and FIGS. 6(c) and (d) are sectional views showing modifications of a stroke portion provided at the vibration mechanism.

As shown in FIGS. 6(a) and (b), the dozing preventive device 20 comprises a contacting portion 22 directly contacting with the teeth of a user, a vibration mechanism 23 for vibrating the contacting portion 22, and a housing case 26 for accommodating the contacting portion 22 and the vibration mechanism 23.

The contacting portion 22 includes an engaging portion 22b having a hollow base portion, a main body 22a of deformed profile extending from the front side of the engaging portion 22b, a pair of engaging protrusions 22c provided on the main body 22a. The pair of engaging protrusions 22c are detachable from a corresponding engaging recess 26a provided at the front side of the housing case 26.

As shown in FIGS. 6(a) and (b), the vibration mechanism 23 comprises a driving motor 23a as a driving portion, a rotational shaft 23b transmitting the rotational movement of the driving motor 23a, and a cam 23c provided at and offset from the front end of the rotational shaft 23b. When the rotational shaft 23b rotates, the cam 23c hits the inner wall of the engaging portion 22b, thereby generating a vibration.

When the user turns on the switch, the driving motor 23a is actuated and the rotational shaft 23b rotates. The cam 23c is then rotated within the engaging portion 22b of the contacting portion 22 so as to hit the inner wall of the engaging portion 22b. By this stroke movement of the cam 23c, vibration is generated at the main body 22a of the contacting portion 22. When the main body 22a is brought into contact with the user's teeth, the vibration, i.e., stimulation with a constant wavelength is transmitted through the teeth to the user's brain, thereby preventing the user from sleeping.

Figure 6C:
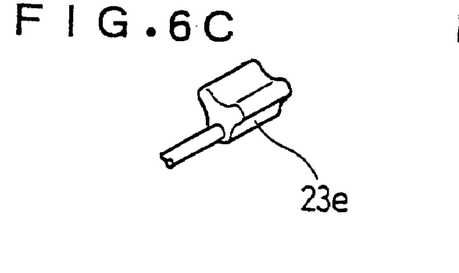
Figure 6D:
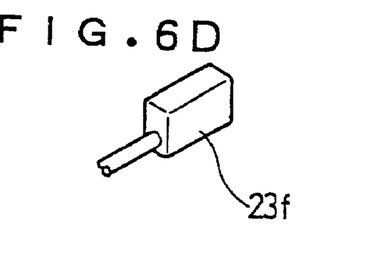

As shown in FIGS. 6(c) and (d), various cams may be employed. FIG. 6 (c) shows a cam having a bifurcated impacting portion 23e, and FIG. 6(d) shows a cam having a rectangular-shaped impacting portion 23f. As long as ensuring reliable stroke against the inner wall of the engaging portion 22b, other cams may be employed.

Figure 7A:
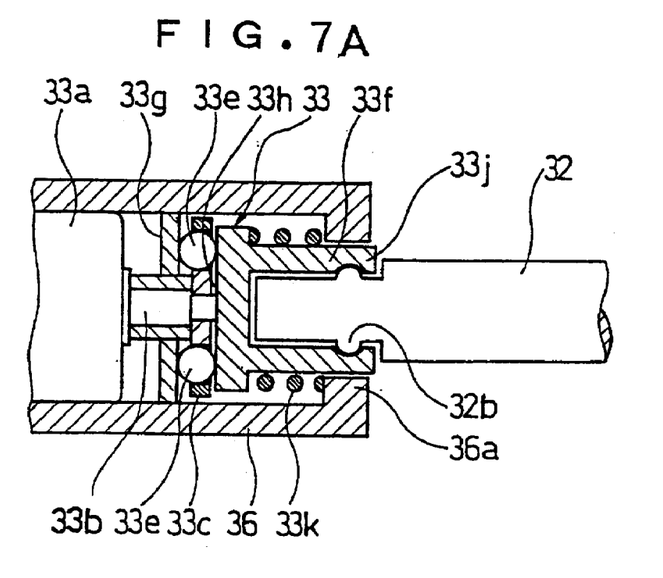
FIG. 7(a) is a sectional view showing the subject construction of another vibration mechanism.
Figure 7B:
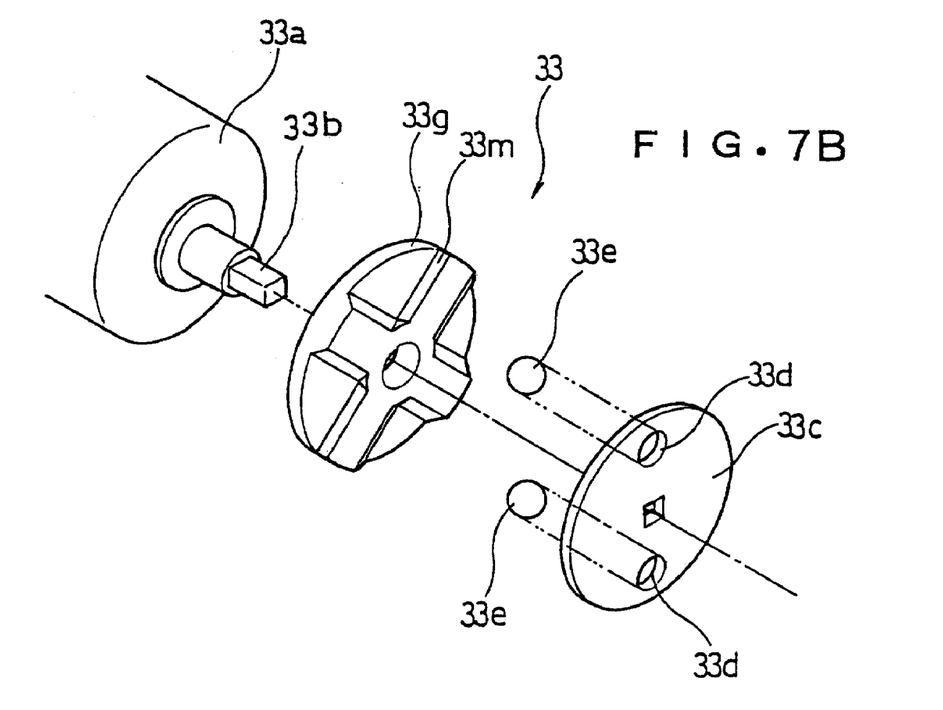
FIG. 7(b) is an exploded perspective view showing the subject construction of the vibration mechanism shown in FIG. 7(a)

Referring now to FIG. 7, sill another vibration mechanism will be described.

As shown in FIGS. 7(a) and (b), the vibration mechanism 33 comprises a driving motor 33a as a driving portion, a rotational shaft 33b for the driving motor 33a, a rotational plate 33c to be rotated by the rotation of the rotational shaft 33b, balls 33e held in the corresponding through apertures 33d of the rotational plate 33c, an engaging block 33f generating a vibration by the interaction with the balls 33e, and a restricting plate 33g for controlling the movement of the balls 33e.

As best seen in FIG. 7(a), an abutting surface 33h is formed at one end of the engaging block 33f for supporting the balls 33e. Provided at the other end of the engaging block 33f remote from the abutting surface 33h is an engaging recess 33j for the engagement with the corresponding engaging protrusions 32 provided on the contacting portion 32b.

A spring 33k as a resilient member is positioned around the engaging block 33f. One end of the spring 33k engages with a fitting portion 36a of the housing case 36, and the other end thereof engages with the reverse surface of the abutting surface 33h. The engaging block 33f is therefore urged inwardly from the fitting portion 36a.

As shown in FIGS. 7(a) and (b), the restricting plate 33g is fixed to the wall of the housing case 36 so that a rugged surface 33m is formed. The balls 33e move along a predetermined locus while supported on the rugged surface 33m. The rotational plate 33c is positioned between the engaging block 33f and the restricting plate 33g. Preferably, diameter of the through apertures 33d is smaller than that of the balls 33e.

When the driving motor 33a is actuated, the rotational plate 33c is rotated through the rotational shaft 33b. The balls 33e held in the through apertures 33d of the rotational plate 33c then move on the rugged surface 33m provided on the restricting plate 33g. When the balls 33e pass on the protrusion on the rugged surface 33m, the engaging block 33f is urged against the resilient force of the spring 33k. Meanwhile, since the rotational plate 33c is urged toward the restricting plate 33g by the resilient force of the spring 33k, the engaging block 33f is urged toward the restricting plate 33g when the balls 33e move on the flat surface of the rugged surface 33m. With such movement of the engaging block 33f, vibration is generated at the front of the contacting portion 32.

When the contacting portion 32 vibrating is brought into contact with the user's teeth, the vibration is transmitted through the teeth to the user's brain, thereby preventing the user from sleeping.

Referring now to FIG. 8, another vibration mechanism will be described.

As shown in FIG. 8(a), the vibration mechanism 43 comprises a coil 43a, a permanent magnet 43b adjacent to the coil 43a, a supporting member 43c for mounting the permanent magnet 43b, a rotational shaft 43d provided at the rear end of the supporting member 43c, and an engaging protrusion 43e as a stroke portion provided at the front end of the supporting member 43c. The engaging protrusion 43e is detachable from the corresponding engaging aperture 42a provided at the base portion of the contacting portion 42. The rotational shaft 43c is rotatably supported by the bearing provided at the housing case.

As shown in FIG. 8(b), the coil 43a is connected to a switching mechanism such as DC servo amplifiers 43g, 43g. When the switching mechanism receives a square wave from the oscillation circuit 43h (including the power supply), an electric current flows alternatively to the coil 43a.

Magnetism of the coil 43a is alternatively changed by the alternative electric current flowing to the coil 43a such that repulsion and attraction are repeated in relation to the south and the north poles of the permanent magnet 43b. The supporting member 43c is alternatively rotated at a predetermined angle through the rotational shaft 43d thereby generating a vibration at the contacting portion 42.

When the contacting portion 42 is brought into contact with the user's teeth, the vibration generated at the contacting portion 42 is transmitted to the user's brain, thereby preventing the user from sleeping. It should be noted that the front end of the contacting portion 42 shown in FIG. 8(c) is bent to have a front angular portion. Since the front angular portion has a different radius of gyration from the base portion of the contacting portion 42, the front angular portion can generate a vibration to the user's teeth upon rotation of the contacting portion 42.

Figure 9:
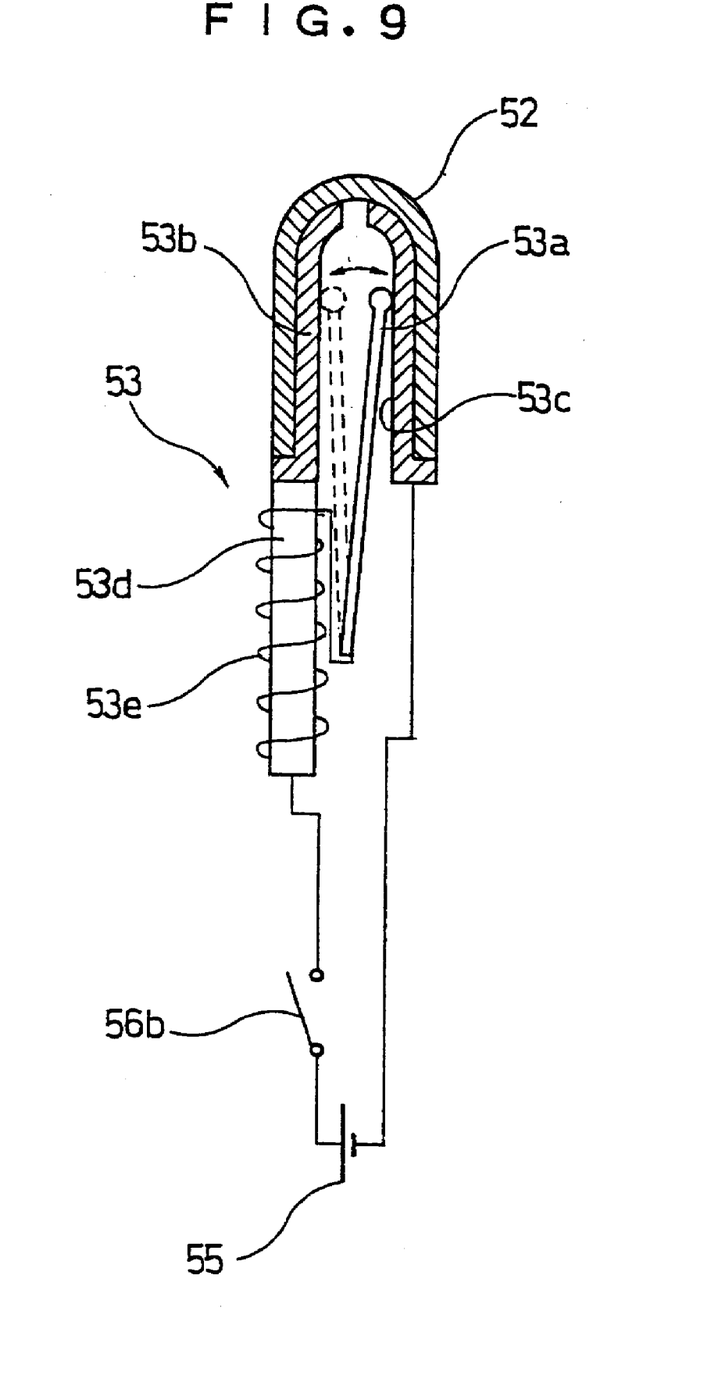
FIG. 9 is a view explaining the principal of another vibration mechanism.

Referring now to FIG. 9, another vibration mechanism will be described.

The vibration mechanism 53 comprises separate metal engaging portions 53b, 53c provided on the inner surface of a contacting portion 52, a stroke portion 53a for alternatively stroking the metal engaging portions 53b, 53c, a metal peace 53d connected to the metal engaging portion 53b, and a coil 53e winding around the metal peace 53d. An electric current flows from the power supply 55 to the coil 53e when the switch 56b is turned on. It should be noted that the stroke portion 53a is urged toward the metal engaging portion 53c.

When turning on the switch 56b, an electric current flows within a circuit formed by the closed loop including the stroke portion 53a and the metal engaging portion 53c. Within this circuit the metal peace 53d functions as an electromagnet and the metal engaging portion 53b connected thereto is magnetized.

When turning on the switch 56b, an electric current flows to the coil 53e so that the metal engaging portion 53b becomes an electromagnet. The metal engaging portion 53b thus attracts the stroke portion 53a against the urging force imparted to the stroke portion 53a so that the stroke portion 53a hits the metal engaging portion 53b. Since the circuit formed by the closed loop is cut off as soon as the stroke portion 53a is disconnected from the metal engaging portion 53b, the metal engaging portion 53b does not function as an electromagnet. The stroke portion 53a is therefore urged toward the metal engaging portion 53c so as to hit the other metal engaging portion 53c.

When the stroke portion 53a contacts to the metal engaging portion 53c, the circuit is again formed. The stroke portion 53a is thus attracted to the metal engaging portion 53b, which functions as an electromagnet. Vibration is generated at the contacting portion 52 by this repeated on-and-off action of the stroke portion 53a.

Since the contacting portion 52 reciprocally vibrates to the direction perpendicular to the axis of the dozing preventive device, when the contacting portion 52 is brought into contact with the teeth of the user, the vibration is transmitted through the teeth to the user's brain.

Figure 10:
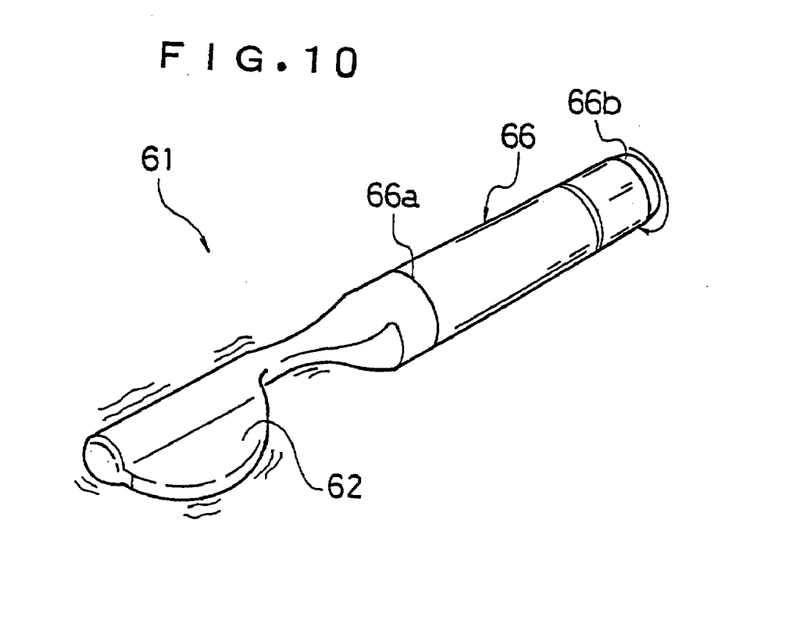
FIG. 10 is a perspective view showing another dozing preventive device according to the present invention.
Figure 11:
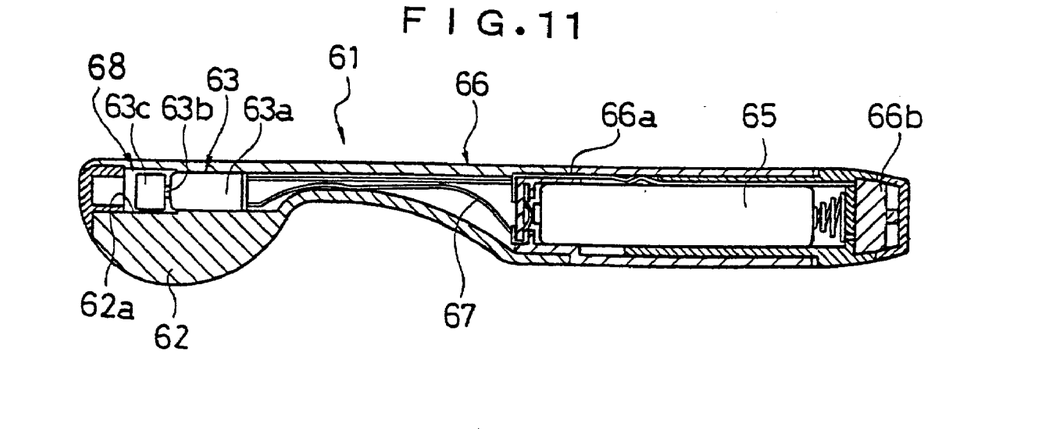
FIG. 11 is a sectional view of the dozing preventive device shown in FIG. 10.
Figure 12:
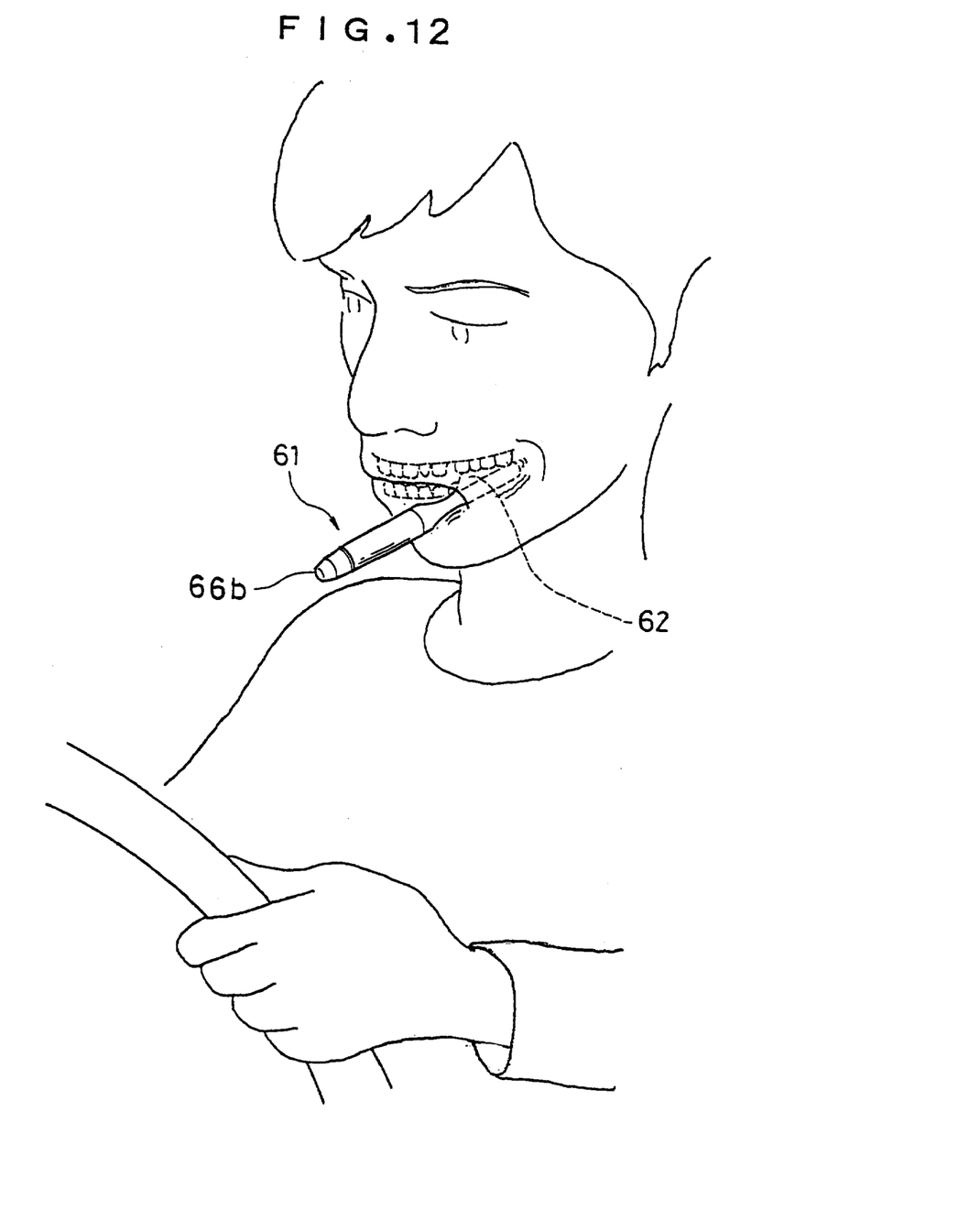
FIG. 12 is a perspective view explaining the state of use of the dozing preventive device shown in FIG. 10.

Referring now to FIGS. 10 to 12, another dozing preventive device according to the present invention will be described.

As shown in FIGS. 10 and 11, the dozing preventive device 61 comprises a contacting portion 62 formed at the front of the housing case 66 by deforming a part of the housing case 66, a vibration mechanism accommodated within the accommodation space 68 which is provided at the rear of the contacting portion 62, a power supply 65 for supplying the vibration mechanism 63 with an electric power through a connecting cord 67, and a switch 66b at the rear of the power supply 65.

A vibrating motor is utilized for the vibration mechanism 63. The vibration mechanism 63 includes a driving portion 63a, a rotational shaft 63b rotated by the driving portion 63a, and an offset portion 63c provided at the front end of the rotational shaft 63b. The offset portion 63c is attached to the rotational shaft 63b in such manner that its center of gravity is eccentric from the center of the rotational shaft 63b. Here, the offset portion 63c has a semicircular cross section so that when the rotational shaft 63b rotates, the offset portion 63c is displaced outwardly due to the centrifugal force on the offset portion 63c. Therefore, the vibration mechanism 63 itself vibrates. Such vibration of the vibration mechanism is transmitted to the rear side 62a of the contacting portion 62, thereby the contacting portion 62 vibrates. It should be noted that the offset portion 63c does not hit the rear side 62a of the contacting portion 62 when the rotational shaft 63b is rotated.

The housing case 66 is formed to have a central reduced thickness portion for facilitating the positioning of the contacting portion 62 relative to the user's teeth. The seam joint 66a is formed outwardly from the contacting portion 62 so as not to be positioned in the user's mouth. This is for preventing propagation of bacteria within the seam joint 66a.

Weight distribution of the dozing preventive device 61 is such that the two halves separated by the central reduced thickness portion have the same weight or the half positioned in a user's mouth becomes heavier. Such weight distribution is advantageous since the dozing preventive device 61 is self-balanced in the user's mouth without biting its contacting portion 62.

A connecting fitting may be employed in place of the connecting cord 67 connecting between the power supply 65 and the vibration mechanism 63. Provision of the connecting fitting enables various designs or modifications of the housing case 66 since the accommodation space 68 becomes greater and the vibration generated at the vibration mechanism 63 is securely transmitted to the connecting portion 62.

As shown in FIG. 12, the user first turns on the switch 66b provided at the rear end of the dozing preventive device 61. (Alternatively, the dozing preventive device 61 may be first kept in the user's mouth in advance of actuating the dozing preventive device.)

The user then bites the contacting portion 62 of the dozing preventive device 61 by his teeth, therefore the user does not have to keep the device 61 by his hands. As shown in FIG. 12, since the dozing preventive device 61 is kept in the user's mouth, two-handed operation of the user, such as handling operation while driving becomes available. The vibration generated at the contacting portion 62 is transmitted through the teeth to the user's brain, thereby preventing the user from sleeping.

Vibration generated at the vibration mechanism 3, 13, 23, 33, 43, 53, 63 and transmitted to the contacting portions 2, 12, 22, 32, 42, 52, 62 may be any directional movement such as to-and-fro, up-and-down or rotational movement.

The dozing preventive device has been described to have a combination of a protrusion and a corresponding stroke portion so that continuous or intermittent vibration can be generated. However, a vibrating motor may be employed, in which the stroke portion can be rotatable in offset relation to the rotational shaft. In such configuration, the corresponding protrusion is not required and the stroke portion (offset portion) does not hit the contacting portion when rotating.

INDUSTRIAL APPLICABILITY (1) The user brings the contacting portion of the dozing preventive device to his teeth. Alternatively, he bites the contacting portion of the dozing preventive device between his teeth. When the user turns on the switch, the vibration mechanism generates a vibration which is then transmitted to the contacting portion. The vibration generated is therefore transmitted to the user's brain, thereby preventing the user from sleeping.

In the dozing preventive device, the vibration mechanism and the power supply are accommodated within the housing case substantially in the size of a cigarette. The user can therefore keep the dozing preventive device in his mouth while being involved in a dangerous operation such as driving. This enables the user to carry out his two-handed operation.

Neighboring people are not disturbed since the dozing preventive device does not generate a beep or buzzing sound. Further, the dozing preventive device does not restrict the user when he is involved in a dangerous operation. Also, the dozing preventive device is sanitary since the contacting portion is detachable from the housing case so that the old contacting portion can be replaced with another new contacting portion.

(2) Vibration generated at the vibration mechanism is transmitted to the contacting portion so that the contacting portion reciprocally vibrates in to-and-fro directions (right-and-left, rotational or up-and-down directions). The vibration is transmitted through the user's teeth to his brain, thereby preventing the user from sleeping.

(3) The dozing preventive device comprises the driving portion including a driving motor and a coil, and the driven portion including a rotational shaft and a stoke portion attached thereto. Since the dozing preventive device is simple in its construction and is small in its size, the dozing preventive device is advantageous for a portable use.

(4) Since vibration frequency is variable by the number of protrusions provided at the contacting portion, various contacting portions with different vibration frequency are available. The user can choose a suitable contacting portion depending on his physical conditions.

(5) Since the vibration mechanism is adjacent to the contacting portion, length of the rotational shaft can be reduced. Therefore, a driving motor with lower driving force can be applied. This leads to smaller configuration of the dozing preventive device. Moreover, the user does not have to support the dozing preventive device by his hand, enabling two-handed operation of the user.

(6) The contacting portion of the dozing preventive device may be formed by deforming one end of the hosing case, and the vibration mechanism is accommodated within the accommodation space at the rear of the contacting portion. Therefore, the number of the parts to be assembled as well as size of the dozing preventive device can be reduced.

The vibration mechanism vibrates within the accommodation space provided at the housing case. The vibration of the vibration mechanism is transmitted to the contacting portion. Since the vibration mechanism is supported within the accommodation space at the rear of the contacting portion, the vibration transmitted to the contacting portion becomes greater. This enables the dozing preventive device with reduced size. Further, since the vibration mechanism itself vibrates and the stroke portion provided at the rotational shaft is rotatable without contacting to the contacting portion, the dozing preventive device is less noisy, compared to the device utilizing impacts between the stroke portion and the contacting portion.

What is claimed is:

1. A dozing preventive device comprising:
   a contacting portion for directly contacting with a set of teeth of a user;
   a vibration mechanism for vibrating the contacting portion;
   a power supply for driving the vibration mechanism; and
   a housing case for accommodating the vibration mechanism and the power supply as well as for supporting the contacting portion
   wherein said vibration mechanism comprises a driven portion having a rotational shaft and a stroke portion provided on the rotational shaft, and a driving portion for driving the rotational shaft and the stroke portion, said contacting portion being provided with a plurality of protrusions for intermittent contact with said driven stroke portion thereby inducing vibration to said contacting portion and a vibration frequency is determined by a number of said protrusions.

2. A dozing preventive device according to claim 1, wherein said vibration mechanism is positioned within the housing case adjacent to said contacting portion, and in that an electric power supply connector is connected between one end of the vibration mechanism and the power supply.

3. A dozing preventive device according to claim 1, wherein a front end of the housing case is deformed to form the contacting portion, and a rear end of the contacting portion is provided with an accommodation space for said vibration mechanism.

4. A dozing preventing method using the dozing preventive device as claimed in claim 3, wherein said contacting portion with a predetermined vibration frequency is brought into contact with the teeth of a user so that the vibration is transmitted to the user's brain.

5. A dozing preventing method using the dozing preventive device as claimed in claim 1, wherein the stroke portion provided on the rotational shaft continuously or intermittently contacts with the contacting portion during the rotational movement of the rotational shaft, and the contacting portion vibrating is brought into contact with the teeth of a user so that the vibration is transmitted to the user's brain.

6. A dozing preventing method using the dozing preventive device as claimed in claim 1, wherein said contacting portion with a predetermined vibration frequency is brought into contact with the teeth of a user so that the vibration is transmitted to the user's brain.

7. A dozing preventive device comprising:
   a contacting portion for directly contacting with a set of teeth of a user;
   a vibration mechanism for vibrating the contacting portion;
   a power supply for driving the vibration mechanism; and
   a housing case for accommodating the vibration mechanism and the power supply as well as for supporting the contacting portion
   wherein said vibration mechanism comprises a driven portion having a rotational shaft and a stroke portion provided on the rotational shaft, and a driving portion for driving the rotational shaft and the stroke portion, said contacting portion being provided with a plurality of protrusions for intermittent contact with said driven stroke portion thereby inducing vibration to said contacting portion and a vibration frequency is determined by the number of said protrusions.

8. The dozing preventive device according to claim 7, wherein a front end of the housing case is deformed to form said contacting portion, and a rear end of the contacting portion is provided with an accommodation space for said vibration mechanism.

9. A dozing preventing method using the dozing preventive device as claimed in claim 8, wherein said contacting portion with a predetermined vibration frequency is brought into contact with the teeth of a user so that the vibration is transmitted to the user's brain.

10. A dozing preventing method using the dozing preventive device as claimed in claim 7, wherein said contacting portion with a predetermined vibration frequency is brought into contact with the teeth of a user so that the vibration is transmitted to the user's brain.

11. A dozing preventing method using the dozing preventive device as claimed in claim 7, wherein the stroke portion provided on the rotational shaft being one of continuously and intermittently in contact with the contacting portion during the rotational movement of the rotational shaft, and the contacting portion vibration is brought into contact with the teeth of a user so that the vibration is transmitted to the user's brain.

\* \* \* \* \*